US008864702B2

(12) United States Patent
Chazot et al.

(10) Patent No.: US 8,864,702 B2
(45) Date of Patent: Oct. 21, 2014

(54) SYSTEM FOR CONTROLLING MEANS FOR INJECTION OF ANESTHETICS OR SEDATIVES

(75) Inventors: Thierry Chazot, Groslay (FR); Ngai Liu, Paris (FR); Bernard Trillat, Paris (FR)

(73) Assignee: Hopital Foch, Suresne Cedex (FR)

( * ) Notice: Subject to any disclaimer, the term of this patent is extended or adjusted under 35 U.S.C. 154(b) by 347 days.

(21) Appl. No.: 13/144,921

(22) PCT Filed: Dec. 4, 2009

(86) PCT No.: PCT/FR2009/052411
§ 371 (c)(1),
(2), (4) Date: Aug. 22, 2011

(87) PCT Pub. No.: WO2010/081946
PCT Pub. Date: Jul. 22, 2010

(65) Prior Publication Data
US 2011/0295196 A1    Dec. 1, 2011

(30) Foreign Application Priority Data

Jan. 15, 2009 (FR) .................................... 09 50215

(51) Int. Cl.
*A61M 31/00* (2006.01)
*A61M 5/172* (2006.01)

(52) U.S. Cl.
CPC ....... *A61M 5/1723* (2013.01); *A61M 2202/048* (2013.01); *A61M 2230/10* (2013.01)
USPC ........................................................ 604/66

(58) Field of Classification Search
CPC .............. A61M 5/007; A61M 5/1723; A61M 2230/10; A61M 2202/048
USPC ................................ 604/65–67, 500; 600/544
See application file for complete search history.

(56) References Cited

U.S. PATENT DOCUMENTS

| 6,631,291 B2 * | 10/2003 | Viertio-Oja et al. .......... 600/544 |
| 6,801,803 B2 * | 10/2004 | Viertio-Oja ................... 600/544 |
| 7,089,927 B2 * | 8/2006 | John et al. ................ 128/200.24 |
| 7,220,240 B2 * | 5/2007 | Struys et al. .................... 604/65 |
| 7,447,541 B2 * | 11/2008 | Huiku et al. .................. 600/544 |
| RE41,291 E * | 4/2010 | Viertio-Oja et al. .......... 600/544 |

(Continued)

FOREIGN PATENT DOCUMENTS

| JP | 1547631 A | 6/2005 |
| WO | WO 2008/059289 A2 | 5/2008 |
| WO | WO 2008/086624 A1 | 7/2008 |

*Primary Examiner* — Aarti B Berdichevsky
(74) *Attorney, Agent, or Firm* — Knobbe, Martens, Olson & Bear, LLP

(57) ABSTRACT

A system comprising means for obtaining a signal representative of the electrocortical activity of the patient, means for analyzing this signal in order to derive from it a signal of depth of anaesthesia, means for monitoring the value and development over time of this signal of depth of anaesthesia, these means being associated with means for calculation of control commands of the injection means, in order to regulate automatically in closed loop the signal of depth of anaesthesia in a predetermined range around a target value, and in that the means for injection of anaesthetics comprise first means for injection of a hypnotic that receive control commands at a first frequency, and second means for injection of a morphinomimetic that receive control commands at a second frequency higher than the first frequency.

18 Claims, 2 Drawing Sheets

(56) References Cited

U.S. PATENT DOCUMENTS

| | | | |
|---|---|---|---|
| 7,783,343 B2 * | 8/2010 | Sarkela et al. | 600/545 |
| 8,512,273 B2 * | 8/2013 | Rantala et al. | 604/23 |
| 2002/0082513 A1 * | 6/2002 | Ennen et al. | 600/544 |
| 2003/0051737 A1 | 3/2003 | Hickle et al. | |
| 2004/0079372 A1 | 4/2004 | John et al. | |
| 2006/0009733 A1 * | 1/2006 | Martin | 604/65 |
| 2006/0058700 A1 * | 3/2006 | Marro et al. | 600/554 |
| 2006/0217628 A1 * | 9/2006 | Huiku | 600/544 |
| 2007/0010756 A1 | 1/2007 | Viertio-Oja et al. | |
| 2007/0276609 A1 * | 11/2007 | Greenwald | 702/19 |
| 2007/0282251 A1 * | 12/2007 | Barvais et al. | 604/67 |
| 2009/0076339 A1 * | 3/2009 | Quintin et al. | 600/301 |
| 2009/0118697 A1 * | 5/2009 | Martin | 604/503 |
| 2009/0124867 A1 * | 5/2009 | Hirsh et al. | 600/301 |
| 2009/0275853 A1 * | 11/2009 | Sarkela | 600/544 |

* cited by examiner

| Type of induction | Type A | | | | Type B | | | | Type C | | | | Type D | | | |
|---|---|---|---|---|---|---|---|---|---|---|---|---|---|---|---|---|
| Stages | P1 | P2 | P3 | P4 | P1 | P2 | P3 | P4 | P1 | P2 | P3 | P4 | P1 | P2 | P3 | P4 |
| Index target value | 65 | 56 | 54 | 52 | 65 | 60 | 55 | 52 | 70 | 63 | 58 | 52 | 68 | 64 | 58 | 55 |
| AFB for hypnotic agent | 50 | 90 | 100 | 100 | 55 | 90 | 100 | 100 | 70 | 100 | 100 | 100 | 70 | 100 | 100 | 100 |
| AFB for morphinomimetic agent | 35 | 45 | 65 | 100 | 50 | 70 | 100 | 100 | 50 | 70 | 75 | 100 | 50 | 70 | 75 | 100 |
| Lower target of hypnotic agent (µg/mL) | 1.3 | 1 | 1.3 | 1.3 | 1.1 | 1 | 1.2 | 1.1 | 0.7 | 1 | 0.7 | 0.7 | 0.7 | 1 | 1 | 0.7 |
| Lower target of analgesic agent (ng/mL) | 5 | 2 | 2 | 2 | 4.5 | 2 | 2 | 2 | 4 | 1 | 1 | 2 | 3 | 1 | 1 | 2 |
| Upper target of analgesic agent (ng/mL) | 12 | 12 | 12 | 12 | 12 | 12 | 12 | 12 | 10 | 10 | 10 | 10 | 10 | 10 | 10 | 10 |
| AFB Coefficient of hypnotic agent | 90 | 65 | 60 | 50 | 90 | 65 | 60 | 50 | 90 | 65 | 60 | 50 | 90 | 65 | 60 | 50 |
| AFB Coefficient of analgesic agent | 92 | 85 | 75 | 70 | 93 | 86 | 76 | 72 | 94 | 87 | 77 | 74 | 95 | 88 | 78 | 75 |
| Additional waiting time for hypnotic agent (s) | 120 | 100 | 50 | 30 | 120 | 100 | 50 | 30 | 90 | 120 | 50 | 60 | 90 | 120 | 50 | 60 |
| Additional waiting time for analgesic agent (s) | 30 | 35 | 45 | 60 | 30 | 35 | 45 | 60 | 30 | 35 | 45 | 60 | 30 | 35 | 45 | 60 |

FIG.2

SYSTEM FOR CONTROLLING MEANS FOR INJECTION OF ANESTHETICS OR SEDATIVES

FIELD OF THE INVENTION

The present invention concerns a system for controlling injectors configured to inject into a patient anesthetic or sedative agents via intravenous anesthesia or sedation mode that is concentration or mass flow target-controlled, with a view to inducing and maintaining this anesthesia or this sedation.

BACKGROUND OF THE INVENTION

A general anesthesia for surgical procedure can be defined as a reversible condition in which the patient must be unconscious through the use of a hypnotic agent, relieved of pain through the use of a morphinomimetic agent and whose muscles must be relaxed through the use of curares which facilitate surgical procedure.

This general anesthesia is obtained by inhaling a gas or via intravenous injection of anesthetic agents, or a combination thereof.

The use of intravenous anesthetic agents alone is usual practice. The evaluation of the depth of anesthesia or the dose adjustment of the anesthetic agents is performed using clinical or paraclinical criteria.

At the current time, the dose adjustment of anesthetic agents is performed in relation to somatic changes (movements) or the autonomic nervous system (tachycardia, hypertension, sweating, pupil size) which are caused by surgery or which are an indication of drug under-dosing.

However, the clinical signs are not always specific or may be absent. Movements are no longer a reliable criterion when a curare is used.

Cardiovascular changes are not specific to the anesthetic agents used and may be related to surgery (bleeding, vessel clamping . . . ) or to the patient (high blood pressure, cardiovascular treatments . . . ).

Target-controlled intravenous anesthesia also called TCI (target-controlled infusion) is a method used for the titration of the injected hypnotic agent or morphinomimetic agent.

This method consists of using a pharmacokinetic model of the agent which calculates a plasma concentration and/or <<effect site>> concentration i.e. in the cerebral region, on the assumption that there is a relationship between the calculated concentration and the effect of the drug.

However, the concentrations calculated by the models have very poor correlation with the clinical condition of the patient, and the use thereof has not shown any improvement in the management of patients undergoing surgery compared with standard usage (i.e. dose-weight infusion) of the same anesthetic agents.

The advantage of TCI tooling is that of providing doctors with the possibility to adapt dosages quicker than with variations expressed as weight concentrations.

The presence of an anesthesiologist therefore remains essential during anesthesia.

However an anesthesiologist is not always available in emergency situations, in military conflict or when the patient cannot be moved.

One method for measuring the depth of anesthesia or the effect of anesthetic agents is to measure the patient's electro-cortical activity or electroencephalogram (EEG).

Anesthetic agents modify the morphology of the EEG signal in a manner specific to each agent. However, only trained electroencephalography technicians are able to detect these changes. EEG measurement has been especially used during research protocols to quantify the effect of anesthetic agents.

Real-time interpretation of EEG changes in the operating room has been facilitated through the introduction of monitors which allow real-time analysis of this EEG signal. These monitors calculate different parameters from the spectral analysis of the EEG and combine these to provide a signal or index of depth of anesthesia.

The BIS monitor by Aspect Medical System Inc. is used to measure the depth of anesthesia by calculating an index number from bispectral EEG analysis. This number varies from 0 to 100, 0 representing an isoelectric tracing or flat and 100 representing a tracing of a patient who is awake. During anesthesia, the recommendation is to hold this number within an interval of 45 and 60 to obtain satisfactory conditions for performing a surgical procedure. With said monitor it is possible to measure the depth of anesthesia and to dose the hypnotic agent.

It has effectively already been proposed to use this BIS index for closed-loop administering of an intravenous hypnotic agent for maintaining anesthesia (see for example document U.S. Pat. No. 7,220,240), or when inducing and maintaining a general anesthesia.

There exists in the state of the art another monitor such as the Entropy monitor for example by Datex-Ohmeda Inc. This monitor quantifies the disorder i.e. the entropy in the EEG signal, this signal for an anesthetised patient being characterised by ample, synchronized and ordered waves, with little disorder and hence low entropy.

It is then sufficient to maintain this index in the 40-60 range to obtain satisfactory conditions for performing surgery. This monitor provides two data items, the first being called "State Entropy (SE)," which measures the depth of hypnosis and the second being called "Response Entropy (RE)," which measures antinociceptive deficiency. This monitor has already been proposed for automated infusion of a hypnotic agent (see for example document U.S. Pat. No. 6,631,291).

SUMMARY OF THE INVENTION

The objective of the invention is to optimise the use of injection systems for injecting anesthetic or sedative agents.

For this purpose, the subject-matter of the invention is a system for controlling injectors configured to inject into a patient anesthetic or sedating agents in intravenous anesthesia or sedation mode that is concentration or mass flow target-controlled, with a view to inducing and maintaining this anesthesia or this sedation, including:
  an electro-cortical activity input for acquiring a signal representing the patient's electro-cortical activity,
  an analysis module for analysing this signal to determine a signal of depth of anesthesia,
  a monitor for monitoring the value and developments over time of this signal of depth of anesthesia, associated with a calculator for calculating control commands of the injectors, for automatic closed-loop regulating of the signal of depth of anesthesia within a predetermined range around a target value,
and in that:
  a first injector is configured to inject a hypnotic agent, wherein the first injector is configured to receive control commands at a first frequency, and a second injector configured to inject a morphinomimetic agent, wherein the second injector is configured to receive control commands at a second frequency higher than the first frequency.

According to other aspects of the invention, the control system comprises one of more of the following characteristics:

it comprises an input interface, so that an operator can input a target value of the signal of depth of anesthesia, wherein the system is configured to determine a default target value, it comprises an operator input interface configured to permit input of type of induction of anesthesia chosen from a group of types of induction differing in the initial concentration of hypnotic agent, the operator input interface configured to permit input of the type of induction is configured to determine the initial concentration of hypnotic agent, with which an initial predetermined concentration of morphinomimetic agent is associated, depending on the type of chosen induction, the calculator is configured to determine intermediate target values of the signal of depth of anesthesia, to define stages during the induction phase, the calculator is adapted to determine three intermediate values for stages of anesthesia, the calculator is configured to limit and/or inhibit control commands in reverse direction of the injection of hypnotic agent and morphinomimetic agent, the calculator is adapted to increase the concentration of hypnotic agent after a predetermined number of modifications of the concentration of morphinomimetic agent, to return the signal of depth of anesthesia to within the predetermined range around the target value, the predetermined number of modifications is three, the calculator is adapted to calculate the difference between the current value of the signal of depth of anesthesia and the target value, and to compare this difference with predetermined threshold values, so that if the current value of the signal of depth of anesthesia lies above the target value:

when the difference is lower than a first threshold, priority is given to action on the concentration of morphinomimetic agent through an increase thereof, when the difference is higher than the first threshold and lower than a second threshold, the concentration of morphinomimetic agent is increased and the concentration of hypnotic agent is increased to a small proportion, and when the difference is higher than the second threshold, the concentration of morphinomimetic agent is increased and the concentration of hypnotic agent is increased to a larger proportion, to return the value of the signal of depth of anesthesia to within the predetermined range, the calculator is adapted to calculate the difference between the current value of the signal of depth of anesthesia and the target value, and to compare this difference with predetermined threshold values if the signal is lower than the target value, so that if the current value of the signal of depth of anesthesia is below the target value:

when the difference is lower than a third threshold, priority is given to action on the concentration of morphinomimetic agent by reduction thereof, when the difference is lower than the third threshold and higher than a fifth threshold, the concentration of morphinomimetic agent is reduced and the concentration of hypnotic agent is reduced to a small proportion, and when the difference is lower than the fourth threshold, the concentration of morphinomimetic agent is reduced and the concentration of hypnotic agent is reduced to a larger proportion, to return the value of the signal of depth of anesthesia to within the predetermined range, it is configured to determine upper and lower limit values of the concentrations of hypnotic and morphinomimetic agents, it comprises a manual input interface for the operator to input the upper and lower limit values of the concentrations of hypnotic and morphinomimetic agents, it comprises a deactivator for deactivating the calculator, to allow the operator manually to take over the control of the agent injectors, it is configured to maintain the control commands at their last value before a loss of the signal of electro-cortical activity, it comprises a sound and/or visual alert component to warn the operator in the event of loss of the signal of electro-cortical activity, and the injectors comprise motorised controllers.

BRIEF DESCRIPTION OF THE DRAWINGS

The invention will be better understood on reading the following description given solely by way of example and with reference to the appended drawings in which.

DETAILED DESCRIPTION OF THE PREFERRED EMBODIMENT

Figure 1:
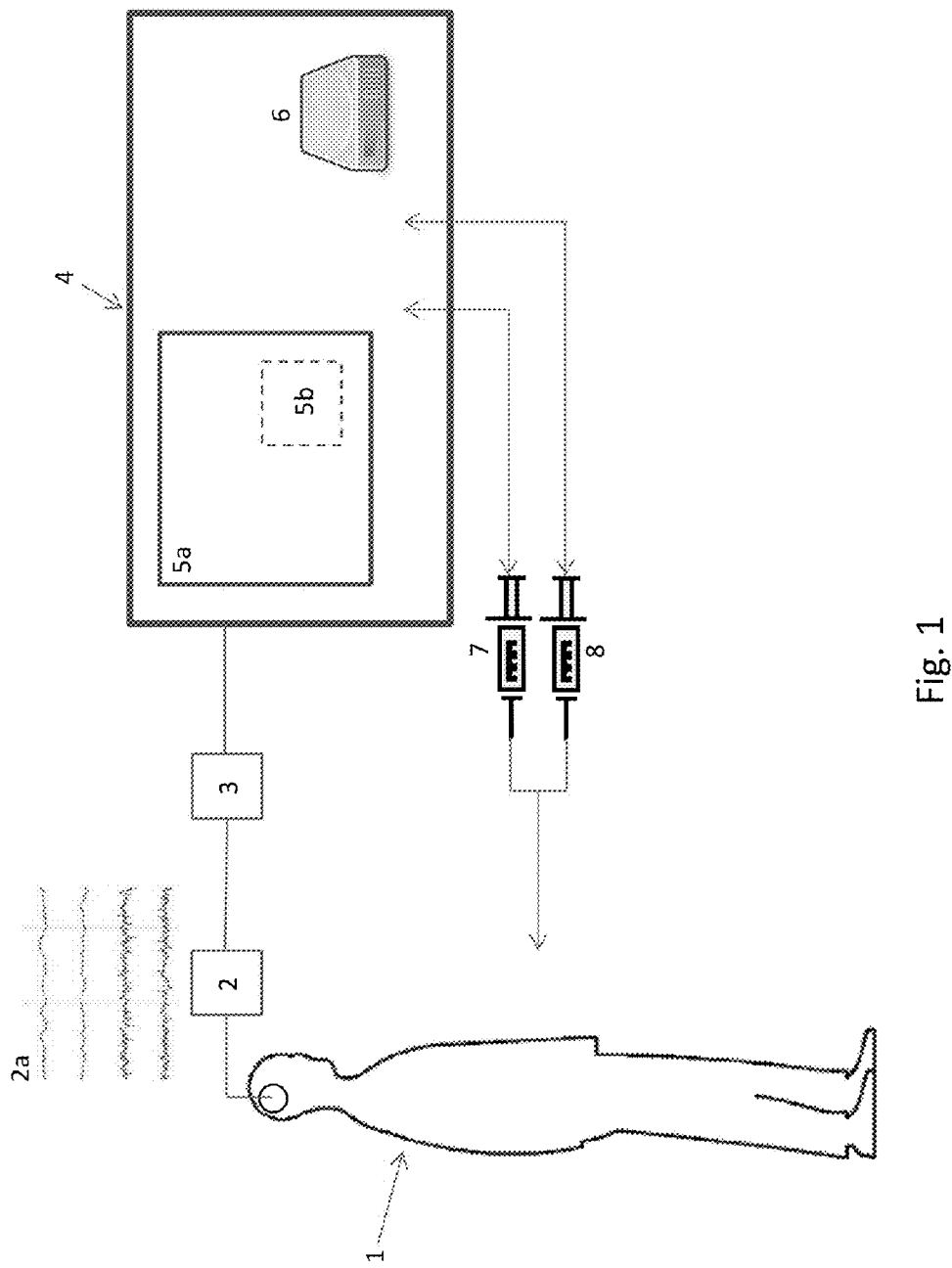
FIG. 1 is a summary schematic of the structure and functioning of a control system according to the invention, and FIG. 2 gives a table of the steps of anesthesia induction.

FIG. 1 effectively illustrates a system for controlling injectors configured to inject into a patient anesthetic or sedation agents in intravenous anesthesia or sedation mode that is concentration or mass flow target-controlled, with a view to inducing and maintaining this anesthesia or this sedation.

In this figure, the patient is designated under general reference 1 and the system comprises an electro-cortical activity input (2) for acquiring a signal representing the patient's electro-cortical activity (2a).

The output of the electro-cortical activity input is connected to an analysis module (3) for analyzing the corresponding signal in order to determine therefrom a signal of depth of anesthesia.

For example, the analysis module may deliver a signal in the form of a BIS index for example or an entropy index, as indicated in the foregoing.

The output of the analysis module is connected to a monitor (4) for monitoring the value and developments over time of this signal of depth of anesthesia, associated with a calculator (5b) for calculating control commands of the injectors, allowing automatic closed-loop regulation of the signal of depth of anesthesia within a predetermined range around a target value.

The monitor is designated under general reference 4 in this figure and for example comprise any suitable computer 5a associated with data storage designated under reference 6.

A first injector, configured to inject a hypnotic agent, receives control commands at a first frequency, designated under general reference 7 in this figure. A second injector, configured to inject a morphinomimetic agent, receives control commands at a second frequency different from the first frequency, designated under general reference 8 in this figure.

In addition, the first and second injectors are configured to feed information back on the quantity of agent administered, of hypnotic agent and morphinomimetic agent respectively, and a controller regularly verifies that the commands are carried out.

It will be noted that the second frequency is higher than the first frequency in the illustrated embodiment.

Therefore, the control system according to the invention allows the controlled injection of hypnotic and morphinomimetic agents from one same BIS or entropy index signal to induce and maintain anesthesia or sedation, whilst maintaining a stable level of depth of anesthesia.

This is achieved using a controller of CLASS type (Closed-Loop Anesthesia Safety System) which controls the injection means in TCI mode using data derived from the monitor after analysis of the patient's EEG activity.

The data delivered by the monitor comprises:
the signal quality index,
the absolute value of the index recorded every five seconds for example,
the EMG value (Electromyogram) or RE value (Response Entropy),
the presence and quantification of BSR (Burst Suppression Ratio),
the variation slope of the index.

Using successive time windows, the computer then measures and calculates from this index:
developments of oscillations in frequency and amplitude,
the time percentage in the 40-60 range,
the time percentage of values lower than 45,
the time percentage of values higher than 55.

The CLASS controller is of Proportional Integral Derivative (PID) controller/regulator type, i.e. a control member allowing closed-loop regulation of an industrial system. PID regulators are the most used in servo-control systems. PIDs allow three simultaneous actions on the error between the objective (or set-point) and the measurement:
proportional action: the error is multiplied by a gain $K_c$ (controller gain),
integral action: the error is integrated over a time interval of $T_i$, called integral time,
derivative action: the error is derived as per a time $T_d$, called derivative time.

If time is a continuous variable, the PID controller is described by the following equation (1):

$$u(t) = K_c e(t) + \frac{K_c}{T_i} e(t) \int_0^t e(t) dt + K_c T_d + K_c T_d \frac{de(t)}{dt} \quad (1)$$

When time becomes a discrete, digital variable (for example if the concentration is maintained constant between two BIS measurements), the PID can be written as per the following equation (2):

$$u(t) = u(t - T_s) + K_c[e(t) - e(t - T_s)] + \quad (2)$$
$$\frac{K_c T_s}{T_i} e(t) + \frac{K_c T_d}{T_s} [e(t) - 2e(t - T_s) + e(t - 2T_s)]$$

where $T_s$ is the time interval between measurements for said digital PID controller.

In these two equations (1) and (2), u(t) is the output of the controller and $e(t) = y_{sp} - y(t)$ is the Index Error where $y_{sp}$ is the objective (known as the set-point).

The controller modifies the target concentration at the effect site, denoted Ce, of the hypnotic agent such as Propofol or of the morphinomimetic agent such as Remifentanil to maintain the BIS at a set-point of 50 for example. The algorithm can be broken down into two terms: amplification of feedback (AFB) and Feed-forward.

The CLASS controller has a cascade structure which integrates the following elements:

1/ The Index Error

The Index Error is calculated every five seconds for example and represents the difference between the measured index and the nominal index i.e. the desired index. This nominal index can be inputted by an operator and then represents the target value of the signal of depth of anesthesia. It can also be determined by means determining a default target value e.g. 50. If the Index Error differs from zero, a modification in the concentration of the agents is carried out after a predetermined waiting time.

2/ Time Between Each Modification

A time period or refractory period between each modification must be observed. This period is initially calculated by the pharmacokinetic model of each anesthetic agent. For example, the Schnider model can be chosen for the hypnotic agent and the Minto model for the morphinomimetic agent. The waiting period between each modification of concentration then depends upon the time needed to reach the concentration at the effect site calculated by the model. Between each modification, the controller waits for the time that is necessary to reach the calculated concentration at the effect site. To this theoretical time a variable additional time period is added, which depends on the last modification of concentration. If the modifications to concentration are small, the equilibrium or stabilising time at the effect site is longer, and an additional time period is added varying from five seconds to two minutes for example.

With regard to the morphinomimetic agent, each command to lower the target value induces an increase in the additional time period and a reduction in the trigger threshold for further lowering. The first command to increase the target value resets the additional time period and the trigger threshold for lowering of the target value.

On the other hand if the Feed-forward is actuated, this has priority and a modification of concentration can be triggered automatically and immediately.

3/ Amplification of the Feedback—AFB

Amplification of feedback is the gain which allows modification of concentration. This correction is possible if the quality index of the signal is higher than 50%.

Amplification of feedback is dependent upon the Index Error, on EMG activity, on the anesthetic agent and on feed-forward. AFB modifies the concentration as per the following formula:

(new concentration)=(current concentration)×(1+Index Error/AFB)

The correction can be expressed as:

$$C_e(t) = C_e(t - T_s)\left[1 - \frac{e(t)}{AFB}\right]$$

where:
−e(t) is the Index Error, where $e(t) = BIS_{sp} - BIS(t)$, and
$T_s$ is the minimum time between two periods of modification of the concentration. It is at least equal to the time needed to reach the peak of the effect of the drug. This time period is adjusted from 5 to 120 seconds depending on the last correction. A previous correction of small amplitude increases the waiting time for the following modification.

If the following are replaced in the preceding equation: $u(t)=C_e(t)$, $y(t)=BIS(t)$ and $y_{sp}=BIS_{sp}$, the correction can be written:

$$u(t) = u(t-T_s)\left[1 - \frac{e(t)}{AFB}\right] \quad (3)$$

The comparison of equations (2) and (3) then allows the remark that the controller of the correction is an integral function and that the gain is a function of type $u(t-T_s)$:

$$\frac{K_c T_d}{T_i} = \frac{C_e(t-T_s)}{AFB} \quad (4)$$

The increase in the concentration of anesthetic agents is greater the higher the Index Error. However, the variations in concentration are limited during decrementing phases thereof to avoid refractory periods of more than three minutes for example. AFB is specific to each agent, to the stage of anesthesia (induction or maintenance), to each Index Error and to concentrations of agents in progress. The determination of AFB is dependent upon the sign and the extent of the Index Error.

4/ Feed-Forward

This function allows amplification of the correction of concentration. In the hierarchy of the CLASS controller, Feed-forward has priority and can act at any time.

This function is inhibited if the quality index of the signal is lower than 50, if the mean BSR percentage (Burst suppression ratio) has been higher than 5% over the last four minutes, and if EMG activity is greater than 47 dB, which is then considered to be an artefact, if amplification of feedback is in progress and if the anesthesia phase is the induction phase.

This function is activated during the maintenance phase of anesthesia, if the measured index is higher than 60 or if the Index Error ($-e(t)$) is higher than 10, if the slope of the index increases by more than 10 points in less than fifteen seconds for example, or if EMG activity exceeds 41 dB for a hypnotic agent such as Propofol and 37 dB for a morphinomimetic agent such as Remifentanil. Finally, this function can be activated by oscillations of the index or of EMG activity.

The condition can then be expressed as $e(t)-2e(t-1)+e(t-2)>10$ with a measurement every five seconds.

When the Feed-forward is activated, a correction of concentration is performed immediately with an AFB proportional to the Index Error and to the current concentration of the agents: $AFB=-e(t).EMG.u(t-T_s)$ where:

$$u(t) = u(t-T_s)\left[1 - \frac{e(t)}{AFB}\right] = u(t-T_s)\left[1 + \frac{1}{EMG \cdot u(t-T_s)}\right],$$

which gives:

$$u(t) = u(t-T_s) + \frac{1}{EMG}$$

In addition, if the current concentration is low, the controller determines a default concentration to avoid modifications that are too small. For example:

if the current concentration of hypnotic agent is lower than 1.3 µg/mL, the activation of this function causes a minimum increase in concentration to a target value of 1.8 µg/mL at the effect site, and if the current concentration of morphinomimetic agent is lower than 4 µg/mL, the activation of the function causes at least an increase to a target value of 4 µg/mL at the effect site.

5/ Rules for Interaction Between the Hypnotic and Morphinomimetic Agents

In the system according to the invention, there are therefore two controllers, one for the hypnotic agent and the other for the morphinomimetic agent. These two controllers are activated at the same time during the induction of anesthesia, after which they function independently.

Since the pharmacokinetic properties of a morphinometic agent of Remifentanil type for example differ from those of a hypnotic agent such as Propofol for example, the waiting period between each modification is shorter, the added waiting times are shorter and the trigger conditions are closer around the target index value for the morphinomimetic agent compared with those of the hypnotic agent. As a result, the modifications of the morphinomimetic agent are generally more frequent than for the hypnotic agent, in the absence of activation of the Feed-forward function.

Also, the rules for interaction are activated to limit and even avoid control decisions and commands in reverse direction of the first and second injection means. Therefore, when the concentration of morphinomimetic agent increases, the controller limits the possibility that the concentration of hypnotic agent decreases. Similarly, when the concentration of morphinomimetic agent decreases, the controller limits the possibility than the concentration of hypnotic agent increases. When it is the concentration of hypnotic agent which increases, the controller limits the possibility that the concentration of morphinomimetic agent decreases. Similarly, if the concentration of hypnotic agent decreases, the controller limits the possibility that the concentration of morphinomimetic agent increases.

Variations that are repeated, or of large amplitude, in the concentration of one of the agents lead to prohibiting reverse variations in the concentration of the other agent by temporarily fixing the lower limit of the concentration of this agent at the current value.

Also, if there are more than three successive positive modifications (increases) in the concentration of morphinomimetic agent, a positive correction in the concentration of hypnotic agent is performed. Evidently a different number of successive modifications can be envisaged.

6/ Administration of the Agents in TCI Mode

The administration of anesthetic agents in target-controlled infusion mode (TCI) is a method that has been used in clinical practice for years and which makes use of an infusion pump associated with a microprocessor. The programme of the microprocessor contains the pharmacokinetic model which models the elimination and metabolism of the drug.

By entering the age, gender, weight and height of the patient and the desired plasma concentration, the integrated programme computes and administers a bolus of the drug needed to obtain the desired concentration.

It also allows a calculated, theoretical concentration to be held stable.

The programme also allows calculation of the theoretical time needed to obtain a new plasma concentration at the effect site.

If the quality index of the signal is lower than 50%, the tool maintains the last chosen concentration. The system then allows the real-time display of the calculated theoretical plasma concentrations and at the effect side, the concentration chosen by the tool, the concentration curves, the waiting time for the next modification when applicable and the mass flow. This then allows calculation of the time needed to reach equilibrium of the chosen target concentration, evaluated by the pharmacokinetic model used.

In the system of the invention, there are in fact two controllers of PID type which have the same structure and of which one controls the concentration of hypnotic agent and the other the concentration of morphinomimetic agent, simultaneously from data derived from the same index signal. In the absence of Feed-forward activation or of rules of interaction, and if the waiting time between two modifications has been observed, the controller can decide to modify a concentration.

Since the time for action given by the pharmacokinetic model is quicker for the morphinomimetic agent such as Remifentanil, the concentrations of this agent are modified more frequently than those of the hypnotic agent such as Propofol. This modification is dependent upon the sign of the Index Error. A positive Index Error causes an increase in concentration and a negative Index Error causes a decrease in concentration.

If the Index Error is lower than ±2 for the morphinomimetic agent and lower than ±3 for the hypnotic agent, no modification is made. Beyond the indicated Index Error values the controller performs a modification. To each Index Error value an AFB is allocated and a specific waiting time for the two agents.

The notion of automatic management of the morphinomimetic agent is based on the fact that small variations in index prefigure larger variations and are attributable to a limited lack of analgesia rather than to deficiency of hypnotic agent. The adjustment parameters have therefore been determined so that the reactivity of the morphinomimetic system is greater than that of the hypnotic system. The number of changes in the concentration of morphinomimetic agent is therefore higher than for the hypnotic agent on account of a shorter refractory period between each modification and a lower trigger threshold. The behaviour of the closed loop of the hypnotic agent is therefore to avoid having an index below 40 or above 60.

The CLASS controller records the data derived from the monitor and the injection means which, for example, may be in the form of motorized means such as electric syringes.

As indicated in the foregoing, the data to be provided when setting the system in operation is the age, height, weight and gender of the patient and the anesthesiologist decides the first concentration of hypnotic agent. The system then calculates the first concentration of morphinomimetic agent. Therefore, with this system it is possible to maintain the index within a range of 40 and 60 for example.

The algorithm integrated in the CLASS controllers comprises two specific parts, one for the induction phase of anesthesia and the other for the maintaining phase thereof. The changeover between the two phases is made automatically.

The system according to the invention allows automatic performing of the induction phase, which is defined as the period between the start of administration of the agents and the maintaining of the EEG signal for at least 30 seconds under the value of 60 for example.

The only decision by the user is therefore to choose the initial concentration of hypnotic agent such as Propofol between 1 and 5 µg/mL. The user in fact chooses a type of anesthesia induction from among a group of induction types which differ in the initial concentration of hypnotic agent. The controller then automatically determines the first concentration of morphinomimetic agent such as Remifentanil in relation to the concentration of hypnotic agent requested by the user, and predetermined according to the chosen type of induction.

For example, four different types of induction can be envisaged: inductions of type A, type B, type C, and type D. The different types of induction differ in:

the value of the initial target concentration of morphinomimetic agent such as Remifentanil, the values of the waiting times after reaching equilibrium of the target concentration of each agent, and the thresholds of the index values which determine a change of stage.

The principle of induction thus designed is based on the idea that the doctor in charge of the patient has means for evaluating the risk related to over-dosage of anesthetic agents during induction. It goes without saying that the higher the risk the smaller the value of the initial target concentration must be. Therefore the initial target concentration value of morphinomimetic agent such as Remifentanil is indexed on the initial target concentration value of hypnotic agent such as Propofol.

Induction of type A can be used for patients not presenting with any major problems and for whom a moderate over-dosage of hypnotic does not give rise to any problem. It is a rapid induction sequence which is requested. The concentration of hypnotic agent such as Propofol is higher than 2.8 µg/mL, the initial concentration of morphinomimetic agent such as Remifentanil being of the order of 5 ng/mL.

Induction of type B can be used for patients presenting with minor problems and for whom it is desired to avoid an over-dosage which may lead to arterial hypotension. In this case, the requested concentration of hypnotic agent such as Propofol may range from 2.4 to 2.8 µg/mL, the initial concentration of morphinomimetic agent such as Remifentanil being of the order of 5 ng/mL.

Induction of type C can be used for fragile patients in whom it is sought to obtain induction with little hemodynamic change. It is a sequence of slow induction. In this case, the requested concentration of hypnotic agent such as Propofol lies between 2.1 and 2.4 µg/mL, the initial concentration of morphinomimetic agent such as Remifentanil being of the order of 4 ng/mL.

Induction of type D can be used for particularly fragile patients or for the management of intensive care patients already sedated. This type of induction is chosen with an initial target concentration of hypnotic agent such as Propofol of 2.1 µg/mL or less.

In addition, the system also comprises means for determining intermediate signal values for depth of anesthesia in order to define stages during the induction phase, for example for the four types of induction.

As input signal the system then uses the signal quality index, the absolute value of the index recorded every five seconds for example, the EMG value and the Index Error.

Depending on the type of induction and the stage of induction, the values for AFB, waiting time and nominal index are specific values.

For example, three intermediate values for stages of anesthesia can be envisaged The objective of the system is therefore to determine a first stage with a nominal index of 80 for example. The measured index is then weighted in relation to EMG activity and the value of the index is reduced if this EMG activity is high in relation to the value of the measured index. The waiting times before a new modification are then fixed. These waiting times vary from 15 to 120 seconds but a maximum waiting time between two variations in the target concentration or per induction stage is fixed.

The table in FIG. 2 summarizes the induction steps for a hypnotic agent such as Propofol and for a morphinomimetic agent such as Remifentanil.

In general:
if the Index Error is negative then the concentration is proportionally reduced by the AFB,
if the Index Error lies between 0 and 10 with a nominal index of 80, then the concentration is not modified and the waiting times are observed as previously, and
if the Index Error is higher than 10, then the concentration of the two agents is increased.

The second stage is guided with a nominal index of 70.

The third stage can be determined with a nominal index of 60 and with rules identical to those for the other stages to wait until expiry of the predetermined waiting times.

In fact, an additional waiting time can be added to the time calculated by the model. This additional waiting time depends on the type of induction.

At the end of the induction phase, which is defined as the period between the start of administration of the anesthetic agents and the maintained value of the signal of depth of anesthesia for at least 30 seconds below a value of 60 for example, the CLASS controller changes over to maintenance phase. The maintenance phase can be described according to observation of the input signal which comprises:
the quality index of the signal,
the absolute value of the index recorded every 5 seconds for example,
the EMG or RE value,
BSR presence and quantification,
the variation slope of the index, and
measurement and calculation from the index, using successive time windows, of:
developments of oscillations in frequency and amplitude (as described above),
the time percentage in the 40-60 range,
the time percentage of values below 45, and
the time percentage of values above 55.
In addition, consideration is also given to:
developments in the targets of the two anesthetic agents per successive time windows, and
the ratio between the current target value of each agent and the maximum allowed value.

Similarly, the time needed to reach equilibrium of the chosen target concentration and the continuous time spent at the lower limit of one or other of the agents can also be recorded.

It is effectively possible to define means for determining upper and lower limit values for concentrations of the agents, these means for example being means for manual input by the operator of the upper and lower limit values.

For example, during use in closed loop, these minimum and maximum values are 1.3 and 5 µg/mL for example for the hypnotic agent such as Propofol, and 3 and 15 ng/mL for the morphinomimetic agent such as Remifentanil. These values also depend on the type of induction. They become smaller from type A towards type D:
from 1.3 to 0.7 µg/mL for the lower limit of the hypnotic agent such as Propofol, and from 3 to 2 ng/mL for the lower limit of morphinomimetic agent such as Remifentanil, and
from 8 to 12 ng/mL for the upper limit of morphinomimetic agent such as Remifentanil, the upper limit of the hypnotic agent such as Propofol remaining at 5 µg/mL.

At any time the user may decide to modify these limit values, and throughout the time of use of the CLASS controller the following are recorded: the time spent at the lower limit of one or other of these agents, the developments in concentrations of the two agents per successive time window and the ratio between the current target value of each agent and the maximum allowed value.

The processing of oscillations is made over a period of four minutes by measuring the frequency and amplitude of BIS oscillations, an oscillation being a sequence of two variations in opposite direction of the BIS over a period of five second (increase then decrease, or the reverse).

If the oscillations are of large amplitude i.e. if the amplitude of oscillation is greater than a first threshold, a fixed increase in the concentration of hypnotic agent is triggered at the third oscillation. The extent of this increase is indexed on the current target of the agent. This increase is smaller the higher the value of the hypnotic agent target value. This variation in the concentration of hypnotic agent is subject to absence of BSR and a low number of index values below the tolerance range. The triggering thereof blocks triggering of the forward feed.

If the oscillations are of small amplitude, three thresholds are defined triggering different actions if they are reached in the time window of four minutes. The processing of the oscillations then consists of determining the agent on which the system acts by comparing the current target value with the maximum allowed target value at the time of the decision for each agent. This attitude is intended to avoid imbalance between the two main anesthetic agents whose action is known to be synergetic. In this case, action is preferably performed on the agent having the lowest ratio of current target value/maximum target value:
if it is the morphinomimetic agent:
at the first threshold reached by the amplitude of oscillation, the concentration of morphinomimetic agent can no longer decrease,
at the second threshold reached, the AFB of the morphinomimetic is reduced to enhance the following reaction, and
at the third threshold, a fixed increase is decided immediately.
if it is the hypnotic agent:
at the first threshold reached, the concentration of hypnotic agent can no longer decrease,
at the second threshold reached, the AFB of the hypnotic is reduced to enhance the following reaction, and
at the third threshold, a fixed increase is immediately decided. Within a time window of four minutes there cannot be more than three triggers of this function.
Amplification of feedback decreases from the first to the third trigger threshold. This function is only triggered if the BSRs are not too high.

The controller then comprises a computer adapted to calculate the difference between the current value of the signal of depth of anesthesia and the target value, and to compare this difference with predetermined threshold values so that, if the current value of the signal of depth of anesthesia is above the target value:

when the difference is lower than a first threshold, priority is given to action on the concentration of morphinomimetic agent through an increase thereof, when the difference is higher than the first threshold and lower than a second threshold, the concentration of morphinomimetic agent is increased and the concentration of hypnotic agent is increased to a small proportion, and when the difference is higher than the second threshold, the concentration of morphinomimetic agent is increased and that of the hypnotic agent is increased to a larger proportion, to return the value of the signal of depth of anesthesia to within the predetermined range.

Similarly, if the current value of the signal of depth of anesthesia is below the target value:

when the difference is lower than a fourth threshold, the controller acts in priority on the concentration of morphinomimetic agent through a reduction thereof, when the difference is lower than the fourth threshold and higher than a fifth threshold, the concentration of morphinomimetic agent is reduced and the concentration of hypnotic agent is reduced to a small proportion, and when the difference is lower than the fifth threshold, the concentration of morphinomimetic agent is reduced and the concentration of hypnotic agent is reduced to a larger proportion, to return the value of the signal of depth of anesthesia to within the predetermined range.

It will therefore be appreciated that different actions can be generated by the CLASS controller, namely:

proportionally increase the target value of one or other of the agents, proportionally reduce the target value of one or other of the agents, increase the waiting time after a modification of the target value, reduce the waiting time after a modification of the target value, modify the hierarchy of actions in progress, increase the value of the nominal index, reduce the value of the nominal index, block the decrementing of the concentration of hypnotic agent such as Propofol, block the decrementing of the concentration of morphinomimetic agent such as Remifentanil, perform a fixed increase in the concentration of hypnotic agent such as Propofol, perform a fixed increase in the concentration of morphinomimetic agent such as Remifentanil, shift the limits of the tolerance range of index values, amplify feedback in relation to basic calculations, and temporarily modify the lower limit for example of the morphinomimetic or hypnotic agent.

Additionally, safety measures are set up. For example, means for deactivating one and/or the other of the means for calculating control commands of the injection means can be envisaged, to enable the operator to take over controlling of the agent injection means manually.

Similarly, maintenance of control commands at their last value before loss of the signal of electro-cortical activity can be envisaged, for example in association with a sound and/or visual alert component to warn the operator in the event of loss of this signal.

At any time, the user can administer anesthetic agents in manual mode.

These different means can be implemented using software programmes integrated in the computer 5.

It will therefore be understood that said system allows the closed-loop, simultaneous administering of a hypnotic agent such as Propofol and of a morphinomimetic agent such as Remifentanil, in servo-controlled fashion from a single signal of the patient's electro-cortical activity.

A CLASS controller allows the induction and maintenance of general anesthesia, sedation during the post-operative period and sedation for patients in intensive care.

As input signal it uses the electro-cortical activity provided by a monitor monitoring for example a bispectral or entropy index, which allows measurement of the depth of anesthesia.

The invention claimed is:

1. System for controlling injectors configured to inject anesthetics or sedatives into a patient via an intravenous anesthesia or sedation mode that is concentration or mass flow target-controlled, for inducing and maintaining this anesthesia or this sedation comprising:

an electro-cortical activity input configured to transfer to the system a signal representing the electro-cortical activity of the patient, an analysis module configured to analyze the signal to determine therefrom a signal of depth of anesthesia, a monitor configured to monitor the value and development over time of this signal of depth of anesthesia, associated a calculator configured to calculate control commands of the injectors, for automatic closed-loop regulating of the signal of depth of anesthesia within a predetermined range around a target value, and wherein a first injector is configured to inject a hypnotic agent, wherein the first injector is configured to receive control commands at a first frequency, and wherein a second injector is configured to inject a morphinomimetic agent, wherein the second injector is configured to receive control commands at a second frequency higher than the first frequency.

2. The control system according to claim 1, further comprising an input interface configured to allow input by an operator of the target value of the signal of depth of anesthesia, wherein the system is configured to determine a default target value.

3. The control system according to claim 1, wherein the calculator is configured to limit and/or inhibit control commands to the injectors in either order.

4. The control system according to claim 1 comprising a deactivator configured to deactivate the calculator, to enable the operator to take over the control of the agent injectors manually.

5. The control system according to claim 1, wherein the injectors comprise motorized controllers.

6. The control system according to claim 1, comprising an operator input interface configured to permit input by an operator of a type of anesthesia induction type based on the initial concentration of hypnotic agent.

7. The control system according to claim 6, wherein the system is configured to determine the initial concentration of hypnotic agent, with which an initial concentration of morphinomimetic agent predetermined according to the type of chosen induction is associated.

8. The control system according to claim 1, wherein the calculator is configured to determine intermediate target values for the signal of depth of anesthesia to define stages during the induction phase.

9. The system according to claim 8, wherein the calculator is adapted to determine three intermediate values for stages of anesthesia.

10. The control system according to claim 1, wherein the calculator is adapted to increase the concentration of hypnotic agent after a determined number of modifications of the concentration of morphinomimetic agent, to return the signal of depth of anesthesia to within the predetermined range around the target value.

11. The control system according to claim 10, wherein the determined number of modifications is equal to three.

12. The control system according to claim 1, wherein the system is configured to determine upper and lower limit values for concentrations of the hypnotic and morphinomimetic agents.

13. The control system according to claim 12, comprising a manual input interface configured for operator input of the upper and lower limit values for concentrations of the hypnotic and morphinomimetic agents.

14. The control system according to claim 1, wherein the system is configured to maintain the control commands at their last value before a loss of the signal of electro-cortical activity.

15. The control system according to claim 14, comprising a sound and/or visual alert component to warn the operator in the event of loss of the signal of electro-cortical activity.

16. A system for controlling an injector of anesthetics or sedatives into a patient via an intravenous anesthesia or sedation mode that is concentration or mass flow target-controlled, for inducing and maintaining this anesthesia or this sedation comprising:
- a detector configured to detect a signal representing the electro-cortical activity of the patient,
- an analyzer configured to detect the signal to determine therefrom a signal of depth of anesthesia,
- a monitor configured to monitor the value and development over time of this signal of depth of anesthesia, associated with a calculator for calculating control commands of the injector, whereby the system is configured to undergo automatic closed-loop regulating of the signal of depth of anesthesia within a predetermined range around a target value, and wherein the injector of anesthetic agents comprise a first injector for injecting a hypnotic agent, said first injector configured to receive control commands at a first frequency, and second injector for injecting a morphinomimetic agent, said second injector configured to receive control commands at a second frequency higher than the first frequency.

17. A method of returning a value of signal depth of anaesthesia to within a predetermined range comprising:
providing the control system according to claim 1, wherein the calculator is adapted to calculate the difference between the current value of the signal of depth of anesthesia and the target value, and to compare this difference with predetermined threshold values, and optionally if the current value of the signal of depth of anesthesia is above the target value:
increasing with priority the concentration of morphinomimetic agent when the difference is lower than a first threshold,
increasing the concentrations of morphinomimetic agent and hypnotic agent, wherein the increase in concentration of hypnotic agent is less than the increase in concentration of morphinomimetic agent, when the difference is higher than the first threshold and lower than a second threshold, or
increasing the concentrations of morphinomimetic agent and hypnotic agent, wherein the increase in the concentration of hypnotic agent is greater than the increase in concentration of morphinomimetic agent when the difference is higher than the second threshold,
wherein the value of the signal of depth of anesthesia is returned to within the predetermined range.

18. A method of returning a value of signal depth of anaesthesia to within a predetermined range comprising:
providing the control system according to claim 1, wherein the calculator is adapted to calculate the difference between the current value of the signal of depth of anesthesia and the target value, and to compare this difference with predetermined threshold values if the signal is lower than the target value, and
optionally, if the current value of the signal of depth of anesthesia is below the target value:
reducing with priority the concentration of morphinomimetic agent when the difference is lower than a third threshold,
reducing the concentration of morphinomimetic agent and hypnotic agent, wherein the reduction in the concentration of hypnotic agent is less than the reduction in concentration of the morphinomimetic agent when the difference is lower than the third threshold and higher than a fourth threshold, or
reducing the concentration of morphinomimetic agent and hypnotic agent, wherein the reduction in the concentration of hypnotic agent is greater than the reduction in concentration of the morphinomimetic agent when the difference is lower than the fourth threshold,
wherein the value of the signal of depth of anesthesia is returned to within the predetermined range.

* * * * *